US005282482A

United States Patent [19]

Wilk

[11] Patent Number: 5,282,482
[45] Date of Patent: Feb. 1, 1994

[54] PRESSURE RELIEF SUPPORT PAD

[76] Inventor: Peter J. Wilk, 185 West End Ave., New York, N.Y. 10023

[21] Appl. No.: 900,849

[22] Filed: Jun. 18, 1992

[51] Int. Cl.[5] ........................ A61G 15/00; A61F 13/00
[52] U.S. Cl. ...................................... 128/845; 128/889
[58] Field of Search .................... 128/889, 845, 200.14, 128/200.21, 114.1, 25 R; 602/9, 13, 14; 5/630

[56] References Cited

U.S. PATENT DOCUMENTS

| | | | |
|---|---|---|---|
| 3,392,412 | 7/1968 | Aymar . | |
| 3,986,505 | 10/1976 | Power | 128/889 |
| 4,175,297 | 11/1979 | Robbins | 5/447 |
| 4,225,989 | 10/1980 | Corbett | 5/453 |
| 4,662,357 | 5/1987 | Pierce | 128/899 |
| 4,711,375 | 12/1987 | Mäder | 128/200.19 |
| 4,805,603 | 2/1989 | Cumberland | 602/13 |
| 4,932,089 | 6/1990 | Laviero | 5/441 |
| 4,941,478 | 7/1990 | Takeuchi | 128/848 |
| 5,047,007 | 9/1981 | McNichols | 128/898 |
| 5,117,812 | 6/1992 | McWhorter | 128/24 R |

*Primary Examiner*—Michael A. Brown
*Attorney, Agent, or Firm*—R. Neil Sudol; Henry D. Coleman

[57] ABSTRACT

A device for reducing the incidence and severity of dermal conditions such as bedsores and anoxic pressure necrosis of the scalp including a pad disposable on a horizontal support surface, the pad having a cavity or chamber at least partially filled with a fluidic substance. A pressurization component is operatively connected to the pad for shifting the fluidic substance in the cavity, thereby modifying pressure distribution in the cavity. An additional component is operatively connected to the pad for automatically applying a medicinal composition to an upper surface of the pad. This medicine applicator may include an ejector mechanism or a spray nozzle for dispensing a liquid film over the pad. In one embodiment of the invention, the medication applicator is disposed in the same housing as the pressurization component.

15 Claims, 3 Drawing Sheets

PRESSURE RELIEF SUPPORT PAD

BACKGROUND OF THE INVENTION

This invention relates to a device and an associated method for reducing the incidence and severity of dermal conditions such as bedsores and anoxic pressure necrosis of the scalp.

Anoxic pressure necrosis of the scalp is a condition that occurs particularly upon extended surgery and basically results in a bald spot on the patient's head. During surgery, the patient's head usually remains fixed in one position on a table surface. The weight of the head places such pressure on the portion of the scalp in contact with the table surface that the blood supply is cut off, thereby causing the death of skin cells and hair follicles. Although an operating room assisant could periodically manipulate the patient's head to vary the pressure on the back of the head, this procedure is not viewed to be especially useful for several obvious reasons.

Bedsores are painful and possibly dangerous pressure ulcers resulting from continuous lying in a single position on a bed or other support surface. This affliction is particularly common among the patients in nursing homes and hospitals. Although the condition may be reduced by manual moving of the patients, this solution represents a considerable drain on the time and energy of attendants who are in short supply. Other solutions include beds which rock, thereby moving the patients automatically. To introduce such beds throughout a hospital or nursing home would entail a considerable expense, more than many institutions would be willing to undertake.

OBJECTS OF THE INVENTION

An object of the present invention is to provide a device and an associated method for reducing the incidence and severity of dermal conditions such as bedsores and anoxic pressure necrosis of the scalp.

Another object of the present invention is to provide such a device or method which is relatively inexpensive to implement.

Another, more particular, object of the present invention is to provide such a device or method which may be retrofitted to existing beds, to prevent or alleviate bedsores.

Other objects of the present invention will be apparent from the detailed descriptions and drawings included herein.

SUMMARY OF THE INVENTION

A device for reducing the incidence and severity of dermal conditions such as bedsores and anoxic pressure necrosis of the scalp comprises, in accordance with the present invention, a pad disposable on a horizontal support surface, the pad having a cavity at least partially filled with a fluidic substance, and a pressurization component operatively connected to the pad for shifting the fluidic substance in the cavity, thereby modifying pressure distribution in the cavity.

An additional component may be operatively connected to the pad for automatically applying a medicinal composition to an upper surface of the pad. This medicine applicator may include an ejector mechanism or a spray nozzle for dispensing a liquid film over the pad. In one embodiment of the invention, the medicine applicator is disposed in the same housing as the pressurization component.

Pursuant to another feature of the present invention, the pressurization component takes the form of a press mechanism engaging an outer surface of the pad for squeezing the pad to shift the fluidic substance in the cavity. The press mechanism is advantageously located along an edge of the pad.

According to further features of the present invention, the pad includes a plurality of cavities, while the pressurization component includes, for example, valves and manifolds for pressurizing the cavities independently of one another. A timing component may be operatively connected to the pressurization component for inducing the pressurization component to pressurize the cavities in a predetermined sequence.

The fluidic substance is preferably a gel such as silicone gel.

In accordance with a particular embodiment of the present invention, the pressurization component shifts the fluidic substance alternately into and out of the cavity from a reservoir of the fluidic substance.

Where the device is disposable under a patient's head particularly for reducing or eliminating anoxic pressure necrosis of the scalp during surgical operations, the cavity may be one of a plurality of substantially concentric annular cavities.

Similarly, where the device is disposable under the torso of a person lying on a bed for reducing the incidence and severity of bedsores, the cavity may be one of a plurality of cavities disposed in a substantially rectangular array, the pressurization component being connected to the cavities for pressurizing the cavities independently of one another.

A method for reducing the incidence and severity of dermal conditions such as bedsores and anoxic pressure necrosis of the scalp comprises, in accordance with the present invention, the steps of (a) disposing a pad on a horizontal support surface, the pad having a cavity at least partially filled with a fluidic substance, (b) positioning a body part of an individual on the pad, and (c) periodically changing the disposition of the fluidic substance in the cavity, thereby modifying pressure distribution in the cavity.

According to an additional feature of the present invention, the method further comprises the step of automatically applying a medicinal composition to an upper surface of the pad. The medical composition may be sprayed, ejected or otherwise dispensed only onto the upper surface of the pad from a reservoir located in a housing along an edge of the pad. Alternatively, a plurality of ducts may extend through the pad to a plurality of outlets along the upper surface of the pad. Medicine is periodically dispensed through the ducts and out the outlets onto the pad's upper surface.

Pursuant to a particular feature of the present invention, the redistribution of the fluidic substance in the cavity may be implemented by squeezing the pad to shift the fluidic substance in the cavity. Alternatively or additionally, the redistribution of the fluidic substance in the cavity may be accomplished by shifting the fluidic substance alternately into and out of the cavity from a reservoir of the fluidic substance.

According to another feature of the present invention, where the pad includes a plurality of cavities, the cavities are pressurized independently of one another in a predetermined sequence.

A device and an associated method in accordance with the present invention reduce the incidence and severity of dermal conditions such as bedsores and anoxic pressure necrosis of the scalp. In the case of bedsores, the device may be retrofitted to existing beds. Thus, the device and method in accordance with the present invention represent a relatively inexpensive means for reducing the incidence of bedsores in hospitals and nursing homes.

DETAILED DESCRIPTION

Figure 1A:
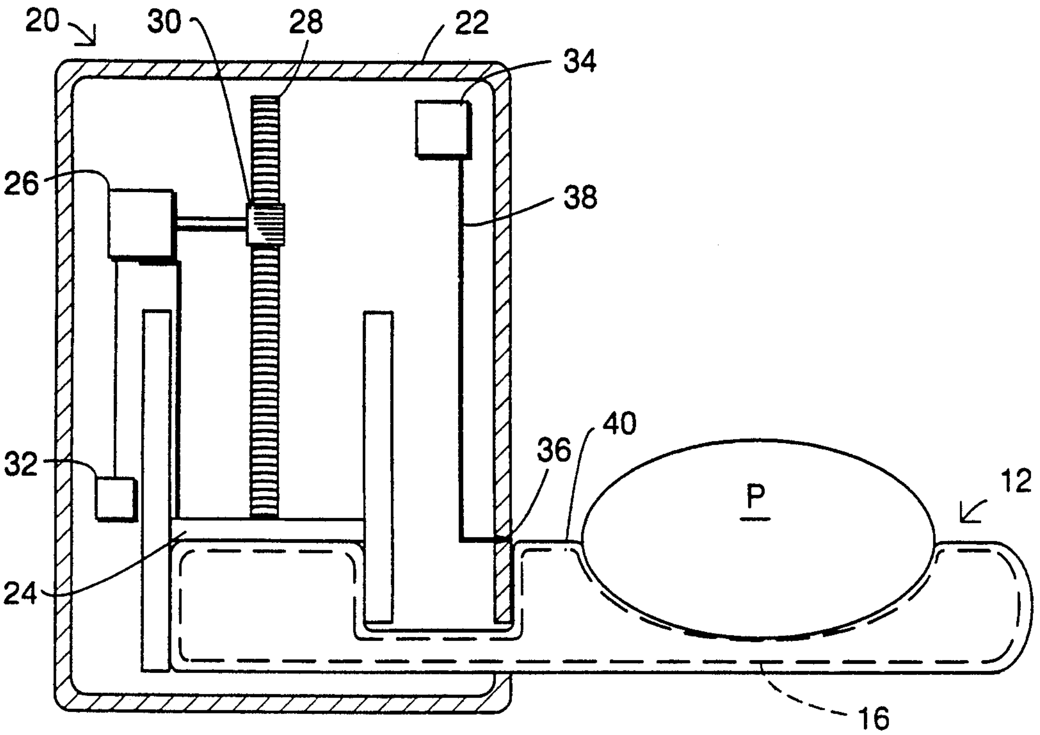
FIG. 1A is a schematic side view, partially in cross-section, of a device for reducing the incidence and/or severity of bedsores, in accordance with the present invention, showing the device in one operative configuration.
Figure 1B:
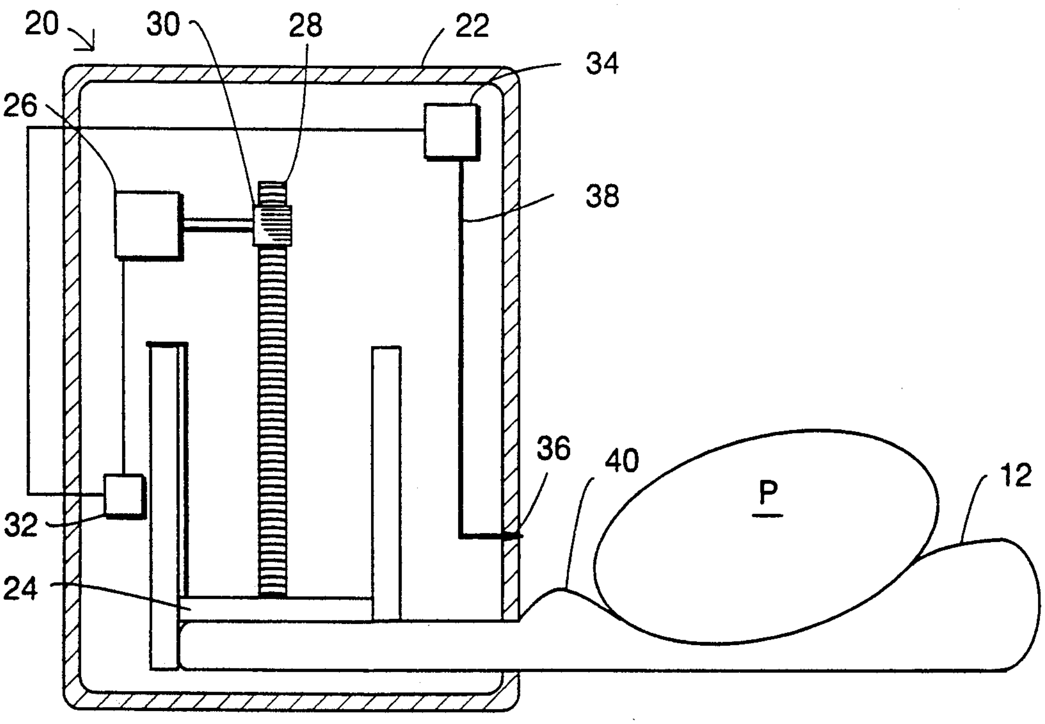
FIG. 1B is a schematic side view, partially in cross-section, of the device of FIG. 1A, showing another operative configuration of the device.
Figure 2:
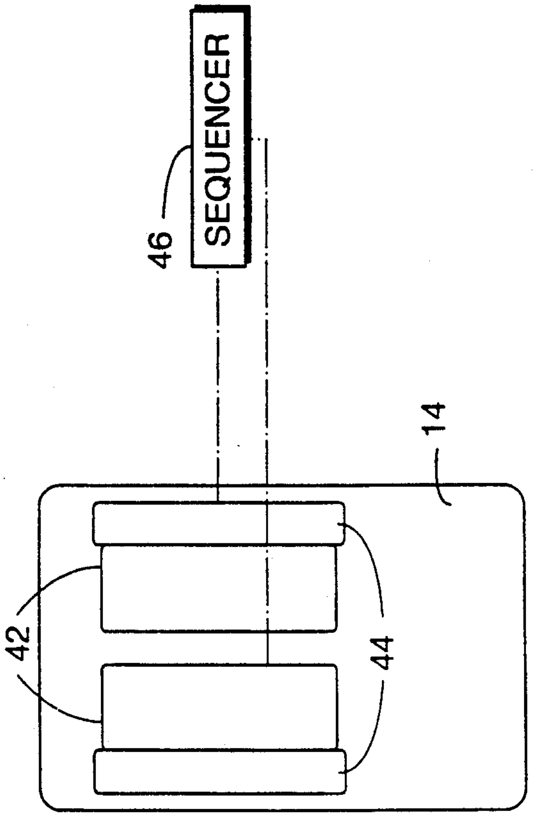
FIG. 2 is a schematic plan view of a bed with a pair of devices such as that illustrated in FIGS. 1A and 1B, with a common timer or sequencer.

As illustrated in FIGS. 1A and 1B, a device for reducing the incidence and/or severity of dermal conditions such as bedsores comprises a pad 12 disposable on a horizontal support surface such as a bed 14 (FIG. 2). Pad 12 has a cavity 16 at least partially filled with a fluidic substance such as silicone gel. A pressurization component 20 is operatively connected to pad 12 for shifting the fluidic substance in cavity 16, thereby modifying pressure distribution in the cavity.

Pressurization component 20 includes a housing 22 containing a press 24 in contact with pad 12. Press 24 is reciprocated alternately into and away from pad 12 by a reversible motor 26 via a rack 28 and pinion 30. Motor 26 is controlled by a timer 32, whereby the fluidic pressure in cavity 16 may be changed and the fluid redistributed in accordance with a predetermined sequence or program.

Housing 22 further contains a pressurized source 34 of a liquid topical medication for pharmaceutically alleviating the effects of bedsores. A nozzle 36 is connected to medicine source 34 via a duct 38. In response to signals from timer 32, pressurized source 34 ejects or sprays an aliquot of the topical medicine onto an upper surface 40 of pad 12.

In response to signals from timer 32, motor 26 rotates pinion 30 and shifts press 24 from a low pressure position in FIG. 1A to a high pressure position depicted in FIG. 1B. This compression or squeezing of an edge of pad 12 forces a redistribution of the fluidic gel substance in cavity 16 from the even distribution of FIG. 1A to the skewed distribution of FIG. 1B. An object such as a patient P resting on pad 12 is slightly turned by the redistribution of fluid or fluid pressure in cavity 16, as depicted schematically in FIG. 1B. It is to be noted that the thickness of pad 12 is greatly magnified in FIGS. 1A and 1B. In addition, the size of pressurization component 20 is enlarged relative to schematically represented patient P.

As illustrated in FIG. 2, a plurality of essentially identical pads 42 with the attendant pressurization components 44 along longitudinal edges may be disposed on a bed 14 along opposite sides thereof. A patient (not shown) is placed on bed 14 so that the patient rests partially on both pads 42. A common sequencer or timing control unit 46 is operatively connected to pressurization components 44 for coordinating the pressurization or compression of pads 42 to gently rock the patient from side to side.

It is to be noted that sequencer 46, as well as timer 32, may be provided with an input element such as a keypad (not shown) for programming the sequencer or timer to implement a predetermined rate and magnitude of rocking or pressure relief.

Figure 3:
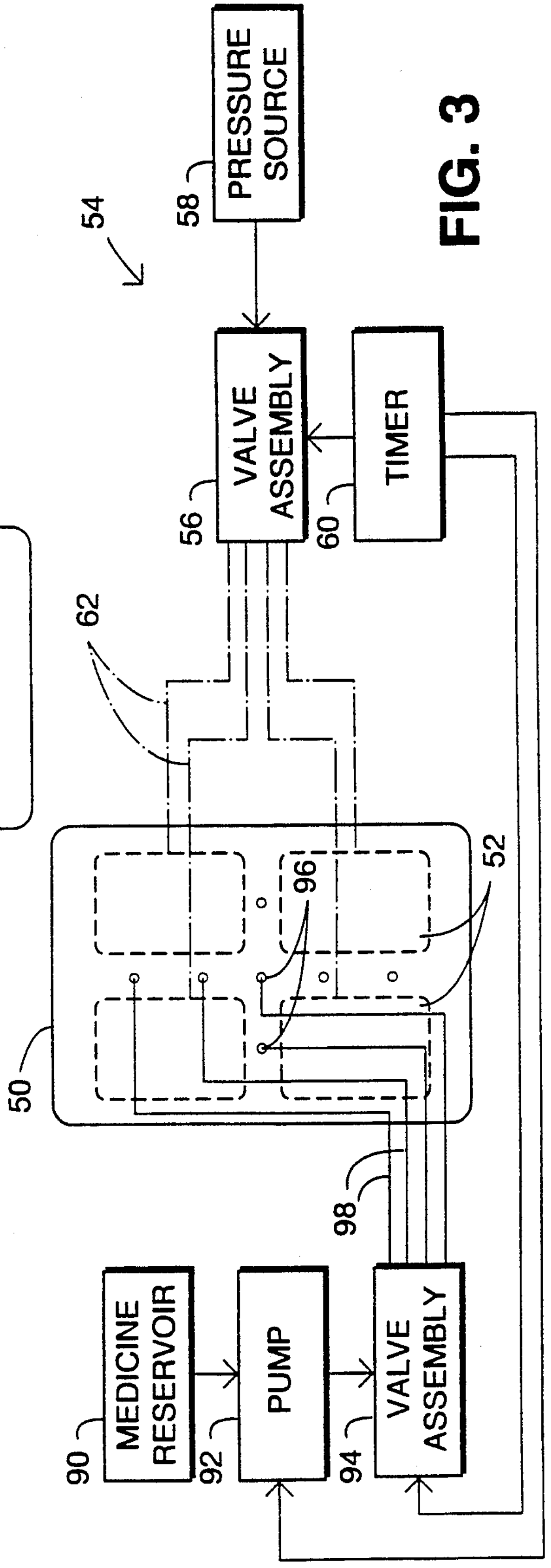
FIG. 3 is partially a schematic plan view and partially a block diagram of another device in accordance with the present invention, for reducing the incidence and/or severity of bed-sores.

As illustrated in FIG. 3, another device for reducing the incidence and/or severity of dermal conditions such as bedsores comprises a pad 50 provided with a plurality of pressurization chambers or cavities 52. A pressurization component 54 includes a valve assembly 56, a pressurized source or reservoir 58 of a fluidic substance such as water or gel, and a timer or sequencing control unit 60. Timer 60 is connected to valve assembly 56 for actuating the valve assembly to differentially pressurize chambers 52 pursuant to a predetermined sequence. The sequence may be individually programmed via a keypad or other input device (not shown). Valve assembly 56 is connected to chambers 52 via a manifold of ducts 62, whereby the chambers may be pressurized independently of one another.

Figure 4:
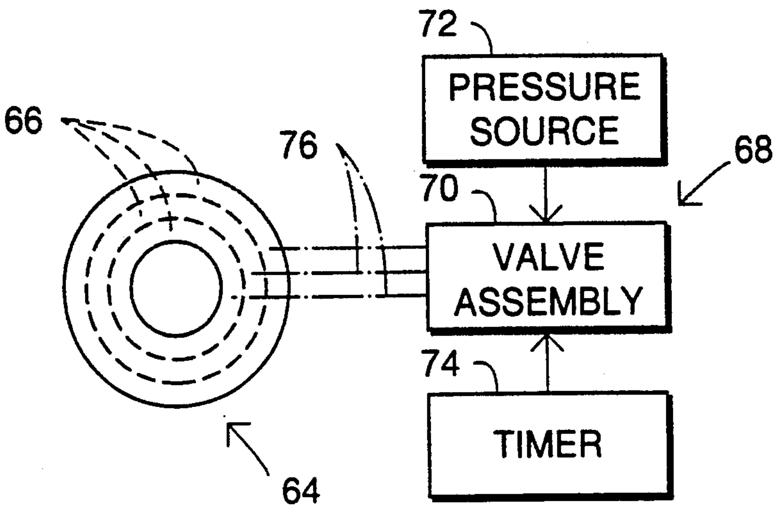
FIG. 4 is partially a schematic plan view and partially a block diagram of a device for reducing or eliminating anoxic pressure necrosis of the scalp, in accordance with the present invention.

As depicted in FIG. 4, an assembly for reducing anoxic pressure necrosis of the scalp particularly during lengthy surgical operations comprises a pad 64 provided with a plurality of annular pressurization chambers or cavities 66. A pressurizing unit 68 includes a valve assembly 70, a pressurized source or reservoir 72 of a fluidic substance, and a timer or sequencing control unit 74. Timer 74 is connected to valve assembly 70 for actuating the valve assembly to differentially pressurize chambers 66 in a predetermined sequence. Valve assembly 70 is connected to chambers 66 via a manifold of ducts 76, whereby the chambers may be pressurized independently of one another.

Figure 5:
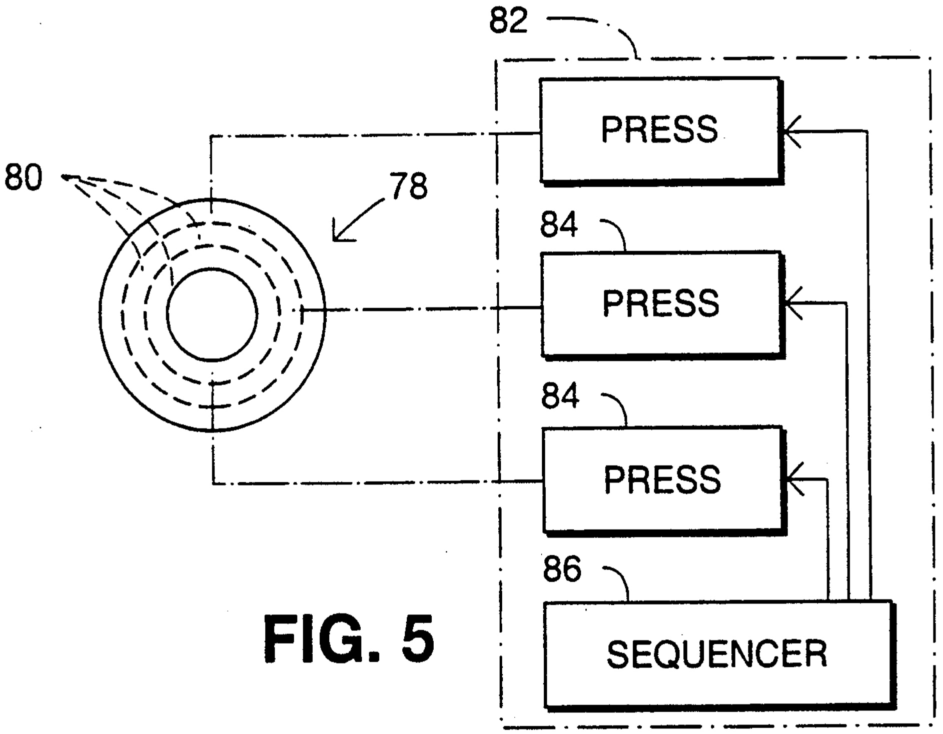
FIG. 5 is partially a schematic plan view and partially a block diagram of a further device for reducing or eliminating anoxic pressure necrosis of the scalp, in accordance with the present invention.

In another embodiment illustrated in FIG. 5, an assembly for reducing anoxic pressure necrosis of the scalp includes a pad 78 provided with a plurality of annular pressurization chambers or cavities 80. A pressurizing unit 82 includes a plurality of presses 84 operatively connected to respective chambers 80 for pressurizing the chambers in a sequence determined by a sequencer 86.

Figure 6:
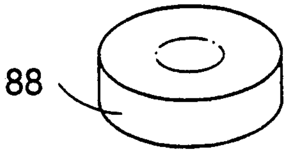
FIG. 6 is a schematic perspective view of an article for reducing or eliminating anoxic pressure necrosis of the scalp, in accordance with the present invention.

As shown in FIG. 6, a simple device for reducing scalp necrosis comprises a cylindrical or annular pad 88 filled with a gel. The pad is placed under a patient's head prior to surgery. As in the bedsore embodiment of FIGS. 1A and 1B, pad 88 may define a single pressure chamber or cavity which may be subjected to a press for inducing a slight rocking of the patient's head.

The embodiments of FIGS. 3–6 may be provided with automatic medication delivery or dispensing componentry. For example, as depicted in FIG. 3, a medication reservoir 90 is coupled to a pump 92 which in turn communciates with a valve assembly 94. Valve assembly 94 is connected to a plurality of outlets 96 in an upper surface of pad 50 via a manifold of ducts or conduits 98. In response to signals from timer 60, pumps 92 and valve assembly 94 direct liquid medication to selected outlets 96.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A device for reducing the incidence and severity of dermal conditions such as bedsores and anoxic pressure necrosis of the scalp, comprising:

a pad disposable on a horizontal support surface, said pad having a cavity at least partially filled with a fluidic substance;

pressurization means operatively connected to said pad for shifting said fluidic substance in said cavity, thereby modifying pressure distribution in said cavity; and means operatively connected to said pad for automatically applying a medicinal composition to an upper surface of said pad.

2. The device defined in claim 1 wherein said means for applying includes an ejector mechanism.

3. The device defined in claim 1 wherein said means for applying is connected to said pressurization means.

4. The device defined in claim 1 wherein said pad includes a plurality of cavities, said pressurization means including means for pressurizing said cavities independently of one another.

5. The device defined in claim 4, further comprising timing means operatively connected to said pressurization means for inducing said pressurization means to pressurize said cavities in a predetermined sequence.

6. The device defined in claim 1, further comprising timing means operatively connected to said pressurization means for controlling operation of said pressurization means.

7. The device defined in claim 1 wherein said fluidic substance is a gel.

8. The device defined in claim 1 wherein said pressurization means shifts said fluidic substance alternately into and out of said cavity from a reservoir of said fluidic substance.

9. The device defined in claim 1 wherein said cavity is one of a plurality of substantially concentric annular cavities, the device being disposable under a patient's head particularly for reducing or eliminating anoxic pressure necrosis of the scalp during surgical operations.

10. The device defined in claim 1 wherein said cavity is one of a plurality of cavities disposed in a substantially rectangular array, said pressurization means being connected to said cavities for pressurizing said cavities independently of one another, the device being disposable under the torso of a person lying on a bed for reducing the incidence and severity of bedsores.

11. A method for reducing the incidence and severity of dermal conditions such as bedsores, comprising the steps of:

disposing a pad on a horizontal support surface, said pad having a plurality of cavities disposed in a substantially planar array parallel to said support surface, said cavities being at least partially filled with a fluidic substance;

positioning a torso of an individual on said pad so that said torso occupies a first predetermined position; and automatically rolling said torso from said first predetermined position to a second predetermined position different from said first predetermined position by pressurizing said cavities independently of one another.

12. The method defined in claim 11 wherein said step of rolling includes the step of squeezing said pad to shift said fluidic substance in said cavities.

13. The method defined in claim 11 wherein said step of rolling includes the step of shifting said fluidic substance alternately into and out of said cavities from a reservoir of said fluidic substance.

14. A device for reducing the incidence and severity of dermal conditions such as bedsores and anoxic pressure necrosis of the scalp, comprising:

a pad disposable on a horizontal support surface, said pad having a cavity at least partially filled with a fluidic substance; and pressurization means operatively connected to said pad for shifting said fluidic substance in said cavity, thereby modifying pressure distribution in said cavity, said pressurization means includes a press mechanism engaging an outer surface of said pad for squeezing said pad to shift said fluidic substance in said cavity.

15. The device defined in claim 14 wherein said pressure mechanism is located along an edge of said pad.

* * * * *